United States Patent [19]

Fixel

[11] 4,372,299

[45] Feb. 8, 1983

[54] ABDUCTION PILLOW WITH STORAGE CAVITY

[76] Inventor: Irving E. Fixel, 111 N. 31st Ave., Hollywood, Fla. 33021

[21] Appl. No.: 299,972

[22] Filed: Sep. 8, 1981

Related U.S. Application Data

[63] Continuation of Ser. No. 75,498, Sep. 13, 1979, abandoned.

[51] Int. Cl.³ .............................................. A61F 5/00
[52] U.S. Cl. .................................... 128/80 A; 128/133
[58] Field of Search ............. 128/68, 80 A, 83, 87 C, 128/133, DIG. 15, 68.1, 134; 5/431, 443

[56] References Cited

U.S. PATENT DOCUMENTS 3,333,286  8/1967  Biolik ........................................ 5/327
3,568,679  3/1971  Reif ..................................... 128/349 R
3,901,228  8/1975  Brown ................................... 128/133

4,135,504  1/1979  Spann ..................................... 128/80 A

*Primary Examiner*—Richard J. Apley
*Assistant Examiner*—J. L. Kruter
*Attorney, Agent, or Firm*—Richard M. Saccocio

[57] ABSTRACT

An improved abduction pillow is disclosed for post-surgical immobilization of a patient's hips and legs. The pillow includes a removable and replaceable portion for sanitary reasons and which permits access to the patient's pelvic area while maintaining hip and leg immobilization. Spare removable portions are stored within the pillow. A soft foam outer covering increases patient comfort and further enhances cleanliness. Catheter channels are provided in the removable portion of precise orientation of a catheter inserted in a patient. The main portion of the pillow is equipped with structural apparatus for attaching convenience items such as a table, tray, radio, etc., to the pillow.

4 Claims, 6 Drawing Figures

ABDUCTION PILLOW WITH STORAGE CAVITY

This application is a continuation of my prior application, Ser. No. 075,498, filed Sept. 13, 1979, now abandoned.

BACKGROUND OF THE INVENTION

1. Field of the Invention

This invention relates in general to the field of post-surgical devices for immobilization of particular portions of a patient's body and in particular to an immobilization device commonly known as an abduction pillow for immobilization of a patient's hips after hip surgery.

2. Description of the Prior Art

After surgery, it is often desirable and sometimes necessary to immobilize certain portions of a person's body so that proper healing is effectuated. The devices or apparatus utilized for such immobilization are sometimes, in general, referred to as "patient positioners". Some of the more commonly used devices are referred to as: head cradle, wheel-chair wedge, face, ear and heel pillow, prone pillow, cock-up splint, wrist restraint, abduction pillow, etc. The names tend to designate the purpose and function of the device. Thus, a wheel-chair wedge comprises a wedge of plastic foam which when placed to the front of a wheel-chair seat under a person will prevent that person from slipping out of the chair. Similarly, a prone pillow allows a patient to lie in a prone position, face down, without hyperextension of the neck.

An abduction pillow is utilized with patients recouperating from total hip surgery or relatively severe hip fractures. The pillow is made from medical foam and generally designed for one-patient use for the duration of treatment. The pillow is formed in the shape of a triangle having a constant thickness of approximately ten inches. The pillow is placed between the legs of a patient with the base of the triangular shape being oriented toward the feet of the patient. By strapping the patient's legs to the pillow, the patient's legs and, therefore, his hips are immobilized in a given position with the feet being spread a comfortable distance. During the period of time that the pillow is used, the patient is, of course, lying in bed and usually on his back. The apex of the triangle opposite the base is located at the pelvic area of the patient.

In the prior art, the abduction pillow is made in one piece. Such one piece construction is unsatisfactory from a hygienic standpoint and from a medical treatment standpoint. Patients requiring total hip surgery are usually elderly and oftentimes do not have firm control of their urinary functions. This lack of control results in urine contamination of the apex portion of the pillow. Since recouperation after total hip surgery is somewhat prolonged, continued urine contamination can cause a significant hygiene problem as well as a generally distasteful overall condition. Any wounds in the pelvic area of a patient often are accompanied by wound drainage which also causes contamination of the pillow. The pillow can be cleaned from time to time to help alleviate these problems; but cleaning is inconvenient, cumbersome, time consuming and is otherwise quite unsatisfactory.

The single piece pillow makes treatment of the urinary tract of a patient or any pelvic area wounds very inconvenient. The apex of the pillow simply interferes with a catheter placed within the patient. Such interference is not conducive to and does not promote proper urine drainage. The apex also interferes with wound dressings making changing of the dressing and treatment of the wound extremely difficult.

One method utilized in the past to attempt to overcome the above problems is the placement of a pillow having a truncated triangular shape between the legs of the patient and away from the patients's pelvic area. This solution has not been satisfactory because the shorter length and nonsupport at the critical pelvic area does not provide adequate hip immobilization and results in a certain amount of patient discomfort.

Abduction pillows are usually not covered. A cloth cover would help maintain cleanliness of the pillow, especially where the pillow is in direct contact with the legs of the patient, but, this has not proved satisfactory because of patient discomfort from heat and moisture build-up. Thus, in the past, uncovered abduction pillows simply get dirty. However, to overcome this problem, the foam from which the pillows are made, are designed to be gas or steam autoclaved. But, this increases costs, causes inconvenience, and is time consuming.

Accordingly, it is an object of the present invention to provide an abduction splint or pillow which can be inexpensively and easily maintained at a high level of cleanliness without the previous attendant problems of patient discomfort from heat and moisture build-up.

Another object of the present invention is to provide an abduction pillow which maximizes hip immobilization while allowing free and noninterfering use of urinary catheters.

Yet another object of the present invention is to provide an abduction pillow which is sufficiently long to result in maximum immobilization of the legs and pelvic area of patients and which is consistent with high standards of hygiene.

BRIEF SUMMARY OF THE INVENTION

In accordance with the above objectives, the present invention comprises an improved abduction pillow for immobilization of a patient's hips after total hip surgery. A triangularly-shaped pillow includes a removable wedge, or perineal portion at the apex of the pillow opposite its base. When in use, the perineal portion is located within a patient's crotch and adjacent to his pelvic area for improved immobilization. The removable wedge portion is provided with one or more cutouts or channels for facilitating the routing, placement, and removal of catheters inserted within the patient. Appropriately shaped cutouts are provided within the main portion of the pillow for storage of one or more spare perineal wedges.

A removable outer cover of medical foam is provided around the periphery of the pillow for immediate contact with a patient's skin or his garments, which cover is easily replaced upon becoming soiled or contaminated. The improved pillow is further provided with structural support members within the main portion of the pillow for attachment thereto and support thereof of convenience items such as a tray, television set, radio, etc.

The inventive pillow is also equipped with internal devices to provide heat and vibration therapy.

BRIEF DESCRIPTION OF THE DRAWINGS

For a fuller understanding of the invention, reference is had to the following description taken in connection with the accompanying drawings in which.

DESCRIPTION OF THE PREFERRED EMBODIMENTS

Figure 1:
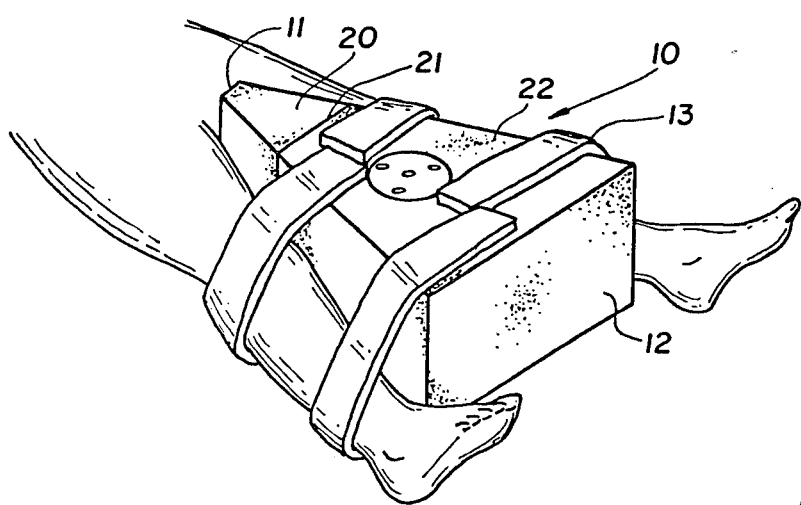
FIG. 1 is an overall isometric view of the improved abduction pillow as applied to a patient for purposes of immobilizing the patient's hips.

Referring now to FIG. 1 of the drawings, the improved abduction pillow 10 is positioned and attached to a patient whose hips are required to be immobilized following total hip surgery. The length of the pillow is such that it extends from a patient's feet to the pelvic area of the patient. While maximum length assures proper hip immobilization, of special importance is the positioning of apex 11 well up within the crotch area of the patient. Apex 11 being the apex opposite the base 12 of the pillow. As will be seen later, the abduction pillow can be firmly entrenched between a patient's legs and in close proximity to his pelvic area without interfering with medical apparatus inserted within the patient such as a catheter for draining his bladder.

The abduction pillow 10 is made from conventional medical foam which may be gas or steam autoclaved for cleaning purposes. Usually an abduction pillow is intended for one-patient use, but this is not a necessary feature. The abduction pillow 10 is conventionally attached to a patient by foam straps 13 which can be secured to the pillow 10 by "velcro" fasteners (not shown). While other types of fasteners can be used, such as buckles and cloth straps, the "velcro" fasteners allow for quick and easy attachment as well as great flexibility in attaining the degree of tightness desired. The use of foam for the pillow 10 and the straps provide for patient comfort and adequate hip immobilization. Usually, the medical foam is uncovered to further provide for patient comfort in that it minimizes heat and moisture build-up. Uncovered foam does, however, create sanitary problems, which the present abduction pillow 10 overcomes and which will be more fully explained hereinafter.

A removable wedge or perineal portion 20 is attached to the end 21 of the pillow 10 opposite the base 12. The perineal portion 20 is conventionally attached to the main portion 22 at end 21 by means of a "velcro" fastener 42 or some other appropriate fastener well known to the art. It is required, however, that wedge portion 20 may be repeatedly removed and reattached without affecting the bond between it and the main portion 22.

The size of wedge portion 20 is not critical; but, to assure proper functioning of the pillow 10, the size of wedge 20 should be approximately one-tenth to one-third of the overall size of the pillow 10. A wedge 20 within the above-stated size and upon being removed from the main portion 22 of the pillow 10 would allow a doctor, nurse, or other medical attendant to care for and clean the patient without affecting immobilization of his legs and hips which, of course, is the prime function of the abduction pillow.

Figure 5:
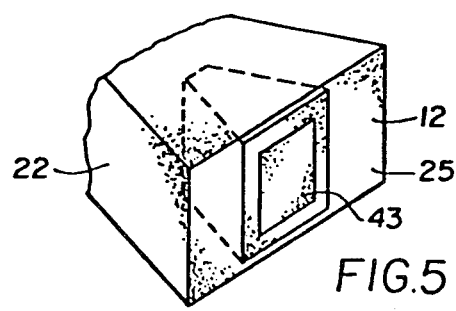
FIG. 5 shows the base of the inventive pillow with a spare perineal wedge in place in the base of the pillow; and, FIG. 6 is a cross-sectional view taken along line 6—6 of FIG. 1 illustrating structural support apparatus for attaching patient convenience items to the inventive pillow.

A spare wedge 25 is shown in place within end 12 of pillow 10 in FIG. 5. Thus, when wedge 20 becomes soiled or otherwise unsuitable for continued use, spare wedge 25 may simply be attached to main portion 22 by fastener 43. Similar spare wedges (not shown) may be positioned within other unused areas of pillow 10.

Figure 3:
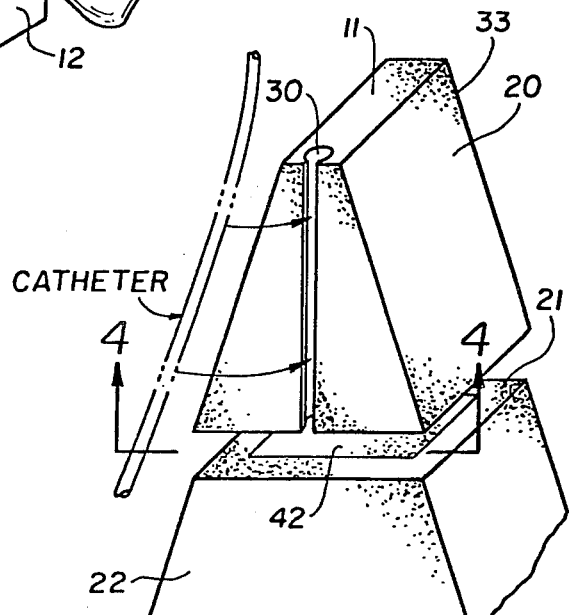
FIG. 3 illustrates the removable perineal wedge separated from the main portion of the pillow and further illustrating a channel for routing of a catheter.
Figure 4:
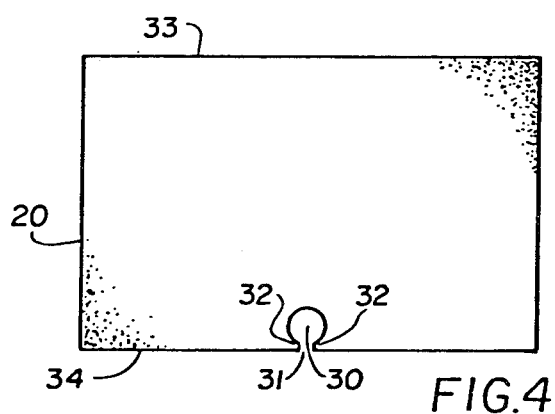
FIG. 4 is a bottom view of the perineal wedge illustrating the cross-sectional shape and a location of a catheter channel.

One or more channels 30 is provided in wedge portion 20 as shown in FIGS. 3 and 4. Channel 30 allows for routing and affixing a catheter from the patient to a drainage receptical. The catheter is shown in phantom in FIG. 3 and is not part of the invention. The catheter is shown for purposes of explanation and is, therefore, not shown in place in the patient nor routed to the drainage receptical. The cross-sectional shape of channel 20 is generally circular. An opening 31 running the length of channel 30 allows the catheter to be placed within channel 30. The lips of channel 30 on either side of opening 31 are flexible in that they are made of foam but are sufficiently resilient so that they serve to lock the catheter in place and thereby prevent an inadvertent dislodgment. In this manner, an assured and desired routing of a catheter is obtained and maintained. Although not shown, a similar channel may be provided along the length of main portion 22 of the pillow 10. In this way the catheter may exit from end 12 of the pillow which would even further assure noninterference between the pillow 10 and the catheter. Well within the contemplation of the invention, and again not shown, is that multiple channels similar to channel 30 may be provided in wedge 20. It is to be realized that the upper and lower surfaces 33 and 34 and wedge 20 may be reversed when the pillow 10 is applied to a patient. However, to assure proper drainage flow through the catheter it is preferable that surface 34 containing channel 30 be oriented horizontally below surface 33. The removable wedge portion 20, when removed, facilitates insertion of the catheter in the patient and facilitates its routing.

Figure 2:
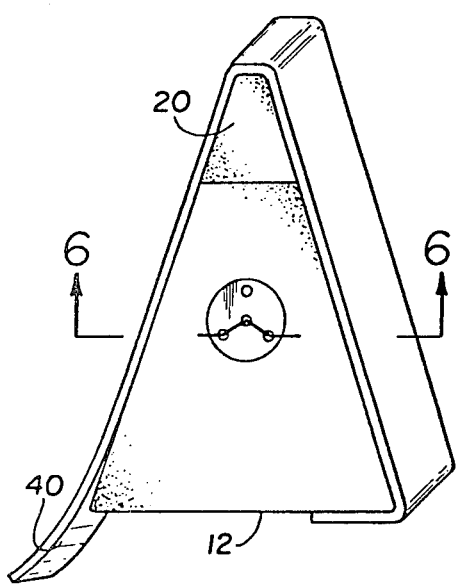
FIG. 2 is the inventive abduction pillow minus the attachment straps for securing the pillow to a patient, illustrating the wrap-around removable cover.

In FIG. 2, a foam outer covering 40 is shown partially in place around the periphery of pillow 10. Covering 40 may be made from soft foam having an approximate thickness of one-half inch. Attachment of covering 40 may again be effectuated by means of "velcro" fasteners. When soiled, covering 40 may be discarded and replaced by another. Covering 40 also allows for reuse of pillow 10 by additional patients.

Figure 6:
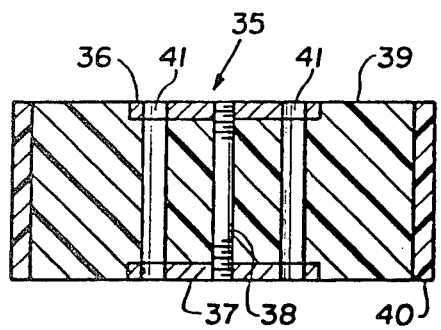

FIG. 6 illustrates, in cross section, convenience support apparatus 35, which apparatus is either permanently or semipermanently attached to pillow 10. In the embodiment shown, the support apparatus 35 comprises an upper 36, and a lower 37 flange attached to each other by connecting member 38. Threads or some other well-known attachment means may be used to secure flanges 36 and 37 to member 38. Cutouts in surfaces 39 and 40 allow for flush fitting of flanges 36 and 37. A number of holes 41 through flanges 36 and 37 and through the foam of pillow 10 comprise recepticals for attaching such items to the pillow 10 as a tray, radio, television, reading stand (all not shown), etc. By modifying these items to be equipped with a number of legs, sized to fit within holes 41, a tray, radio, etc., may be attached to pillow 10.

As an even further improvement, the disclosed abduction pillow is equipped with conventional hydrothermal pads for applying heat therapy to a patient utilizing the pillow. It is envisioned that the hydrothermal pads are imbedded or attached to the sides of the pillow which directly contact the patient's legs. In a similar fashion, standard vibration apparatus may be attached to or imbedded within the pillow for applying vibration therapy to a patient.

From the foregoing, it is apparent that applicant has provided an improved abduction pillow for use with patients requiring hip immobilization.

In the drawings and specification, there has been set forth a preferred embodiment of the invention and although specific items are employed, they are used in a generic and descriptive sense only and not for purposes of limitation. And, while other modifications and changes of the invention may be readily apparent to one skilled in the art, such modifications and changes are intended to be included within the scope of the invention.

I claim:

1. An improved abduction pillow adapted for use with a patient recovering from medical surgery for immobilizing the patient's legs and hips comprising:

a pillow made from foam having a substantially constant thickness, said pillow comprising a first piece having a substantially triangular shape and a second piece having a substantially truncated triangular shape, fastening means for removably connecting said first piece to said second piece whereby said first piece may be disconnected from said second piece and thereafter said first piece may be reconnected to said second piece, a cavity in said second piece having the shape of said first piece, and a spare first piece inserted within said cavity and being removable therefrom, said spare first piece being removably connectable to said truncated end of said second piece.

2. The pillow of claim 1, wherein said first piece includes at least one groove in a surface of said first piece, said groove being substantially oriented with a line representing the height of said triangular shape of said first piece from its base to its apex, said groove having a cross-sectional shape comprising a segment of a circle having a height between the range of the radius of the circle and the diameter of the circle.

3. The pillow of claim 1, including cover means removably attached to said pillow around the periphery thereof for substantially fully covering the substantially rectangular side surfaces of said pillow, said cover means being made from foam comprising a flat substantially rectangular strip of material.

4. The pillow of claim 1, wherein said pillow includes support means for supporting a radio, a tray, a television set, a reading stand, or other like convenience or entertainment apparatus by said pillow, said support means being attached to said pillow, said support means being attached to said second piece, said support means comprising a first support plate and a second support plate, said plates being located opposite each other and separated by the thickness of said second piece of said pillow, said plates being structurally joined by an interconnecting support member.

* * * * *